United States Patent
Li

(10) Patent No.: US 8,263,630 B2
(45) Date of Patent: Sep. 11, 2012

(54) 1,2,3-TRIAZOLES AS 11-BETA HYDROXYSTEROID DEHYDROGENASE TYPE I INHIBITORS

(75) Inventor: James J. Li, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 27 days.

(21) Appl. No.: 12/867,262

(22) PCT Filed: Feb. 11, 2009

(86) PCT No.: PCT/US2009/033753
§ 371 (c)(1),
(2), (4) Date: Aug. 12, 2010

(87) PCT Pub. No.: WO2009/102761
PCT Pub. Date: Aug. 20, 2009

(65) Prior Publication Data
US 2010/0324104 A1 Dec. 23, 2010

Related U.S. Application Data

(60) Provisional application No. 61/027,891, filed on Feb. 12, 2008.

(51) Int. Cl.
*A61K 31/4245* (2006.01)
*A61K 31/4192* (2006.01)
*C07D 413/08* (2006.01)
*C07D 249/06* (2006.01)

(52) U.S. Cl. ......... 514/364; 514/359; 548/131; 548/255

(58) Field of Classification Search .................. None
See application file for complete search history.

(56) References Cited

U.S. PATENT DOCUMENTS

| | | | |
|---|---|---|---|
| 5,081,136 A | 1/1992 | Bertolini et al. |
| 5,411,839 A | 5/1995 | Harder et al. |
| 5,510,362 A | 4/1996 | Matassa et al. |
| 5,552,420 A | 9/1996 | Aldous et al. |
| 5,723,606 A | 3/1998 | Tanaka et al. |
| 5,731,472 A | 3/1998 | Leung et al. |
| 5,849,746 A | 12/1998 | Chambers et al. |
| 5,854,268 A | 12/1998 | Baker et al. |
| 5,861,385 A | 1/1999 | Angerbauer et al. |
| 6,069,141 A | 5/2000 | Barbachyn et al. |
| 6,096,766 A | 8/2000 | Baker et al. |
| 6,248,769 B1 | 6/2001 | Cavalla et al. |
| 6,511,974 B1 | 1/2003 | Dusza et al. |
| 6,576,644 B2 | 6/2003 | Bi et al. |
| 6,936,617 B2 | 8/2005 | Hutchison et al. |
| 7,098,222 B2 | 8/2006 | Altenbach et al. |
| 7,105,558 B2 | 9/2006 | Linney et al. |
| 7,179,581 B2 | 2/2007 | Watanabe et al. |
| 7,226,941 B2 | 6/2007 | Park et al. |
| 7,297,168 B2 | 11/2007 | Murphy et al. |
| 7,319,108 B2 | 1/2008 | Schwink et al. |
| 7,427,612 B2 | 9/2008 | Alberati-Giani et al. |
| 7,572,807 B2 | 8/2009 | Li et al. |
| 7,615,569 B2 | 11/2009 | Fulp et al. |
| 7,767,852 B2 | 8/2010 | Volland et al. |
| 7,838,544 B2 | 11/2010 | Li et al. |
| 2003/0191162 A1 | 10/2003 | Langecker et al. |
| 2004/0248950 A1 | 12/2004 | Ishizuka et al. |
| 2006/0241157 A1 | 10/2006 | Conner et al. |

FOREIGN PATENT DOCUMENTS

| | | |
|---|---|---|
| WO | WO 93/12113 | 6/1993 |
| WO | WO 96/19491 | 6/1996 |
| WO | WO 97/12883 | 4/1997 |
| WO | WO 2004/046141 | 6/2004 |
| WO | WO 2007/023018 | 3/2007 |
| WO | WO 2007/025940 | 3/2007 |
| WO | WO 2007/043581 | 4/2007 |
| WO | WO 2007/096576 | 8/2007 |
| WO | WO 2007/135970 | 11/2007 |
| WO | WO 2007/140174 | 12/2007 |

OTHER PUBLICATIONS

STN search report of compounds in CHEMCATS database (2004).*

* cited by examiner

*Primary Examiner* — Yong Chu
(74) *Attorney, Agent, or Firm* — Terence J. Bogie

(57) ABSTRACT

Novel compounds are provided which are 11-beta-hydroxysteroid dehydrogenase type I inhibitors. 11-beta-hydroxysteroid dehydrogenase type I inhibitors are useful in treating, preventing, or slowing the progression of diseases requiring 11-beta-hydroxysteroid dehydrogenase type I inhibitor therapy. These novel compounds of formula (I): or stereoisomers or pharmaceutically acceptable salts thereof, wherein $R_1$, $R_2$, and $R_3$ are defined herein.

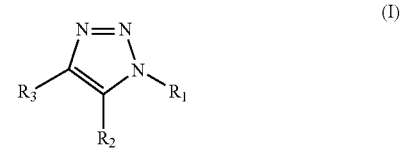

13 Claims, No Drawings

1,2,3-TRIAZOLES AS 11-BETA HYDROXYSTEROID DEHYDROGENASE TYPE I INHIBITORS

BACKGROUND OF THE INVENTION

The steroid hormone cortisol is a key regulator of many physiological processes. However, an excess of cortisol, as occurs in Cushing's Disease, provokes severe metabolic abnormalities including: type 2 diabetes, cardiovascular disease, obesity, and osteoporosis. Many patients with these diseases, however, do not show significant increases in plasma cortisol levels. In addition to plasma cortisol, individual tissues can regulate their glucocorticoid tone via the in situ conversion of inactive cortisone to the active hormone cortisol. Indeed, the normally high plasma concentration of cortisone provides a ready supply of precursor for conversion to cortisol via the intracellular enzyme 11-beta-hydroxysteroid dehydrogenase type I (11beta-HSD1).

11beta-HSD1 is a member of the short chain dehydrogenase superfamily of enzymes. By catalyzing the conversion of cortisone to cortisol, 11beta-HSD1 controls the intracellular glucocorticoid tone according to its expression and activity levels. In this manner, 11beta-HSD1 can determine the overall metabolic status of the organ. 11beta-HSD1 is expressed at high levels in the liver and at lower levels in many metabolically active tissues including the adipose, the CNS, the pancreas, and the pituitary. Taking the example of the liver, it is predicted that high levels of 11beta-HSD1 activity will stimulate gluconeogenesis and overall glucose output. Conversely, reduction of 11beta-HSD1 activity will downregulate gluconeogenesis resulting in lower plasma glucose levels.

Various studies have been conducted that support this hypothesis. For example, transgenic mice expressing 2× the normal level of 11beta-HSD1 in only the adipose tissue show abdominal obesity, hyperglycemia, and insulin resistance. (H. Masuzaki, J. Paterson, H. Shinyama, N. M. Morton, J. J. Mullins, J. R. Seckl, J. S. Flier, "A Transgenic Model of Visceral Obesity and the Metabolic Syndrome", *Science*, 294:2166-2170 (2001). Conversely, when the 11beta-HSD1 gene is ablated by homologous recombination, the resulting mice are resistant to diet induced obesity and the accompanying dysregulation of glucose metabolism (N. M. Morton, J. M. Paterson, H. Masuzaki, M. C. Holmes, B. Staels, C. Fievet, B. R. Walker, J. S. Flier, J. J. Mullings, J. R. Seckl, "Novel Adipose Tissue-Mediated Resistance to Diet-induced Visceral Obesity in 11β-Hydroxysteroid Dehydrogenase Type 1-Deficient Mice", *Diabetes*, 53:931-938 (2004). In addition, treatment of genetic mouse models of obesity and diabetes (ob/ob, db/db and KKAy mice) with a specific inhibitor of 11beta-HSD1 causes a decrease in glucose output from the liver and an overall increase in insulin sensitivity (P. Alberts, C. Nilsson, G. Selen, L. O. M. Engblom, N. H. M. Edling, S. Norling, G. Klingstrom, C. Larsson, M. Forsgren, M. Ashkzari, C. E. Nilsson, M. Fiedler, E. Bergqvist, B. Ohman, E. Bjorkstrand, L. B. Abrahmsen, "Selective Inhibition of 11β-Hydroxysteroid Dehydrogenase Type I Improves Hepatic Insuling Sensitivity in Hyperglycemic Mice Strains", *Endocrinology*, 144:4755-4762 (2003)). Furthermore, inhibitors of 11beta-HSD1 have been shown to be effective in treating metabolic syndrome and atherosclerosis in high fat fed mice (Hermanowski-Vosatka et al., *J. Exp. Med.*, 202(4):517-527 (2002)). Based in part on these studies, it is believed that local control of cortisol levels is important in metabolic diseases in these model systems. In addition, the results of these studies also suggest that inhibition of 11beta-HSD1 will be a viable strategy for treating metabolic diseases such as type 2 diabetes, obesity, and the metabolic syndrome.

Lending further support to this idea are the results of a series of preliminary clinical studies. For example, several reports have shown that adipose tissue from obese individuals has elevated levels of 11beta-HSD1 activity. In addition, studies with carbenoxolone, a natural product derived from licorice that inhibits both 11beta-HSD1 and 11beta-HSD2 (converts cortisol to cortisone in kidney) have shown promising results. A seven day, double blind, placebo controlled, cross over study with carbenoxolone in mildly overweight individuals with type 2 diabetes showed that patients treated with the inhibitor, but not the placebo group, displayed a decrease in hepatic glucose production (R. C. Andrews, O. Rooyackers, B. R. Walker, *J. Clin. Endocrinol. Metab.*, 88:285-291 (2003)). This observation is consistent with the inhibition of 11beta-HSD1 in the liver. The results of these preclinical and early clinical studies strongly support the concept that treatment with a potent and selective inhibitor of 11beta-HSD1 will be an efficacious therapy in patients afflicted with type 2 diabetes, obesity, and the metabolic syndrome.

SUMMARY OF THE INVENTION

In accordance with the present invention, compounds are provided that have the general structure of formula I:

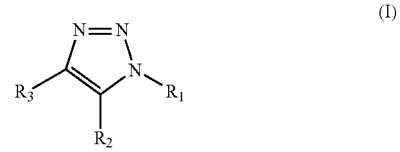

(I)

wherein $R_1$, $R_2$, and $R_3$ are defined below.

The compounds of the present invention inhibit the activity of the enzyme 11-beta-hydroxysteroid dehydrogenase type I. Consequently, the compounds of the present invention may be used in the treatment of multiple diseases or disorders associated with 11-beta-hydroxysteroid dehydrogenase type I, such as diabetes and related conditions, microvascular complications associated with diabetes, the macrovascular complications associated with diabetes, cardiovascular diseases, Metabolic Syndrome and its component conditions, inflammatory diseases and other maladies. Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermittent claudication), abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis, Cushing's Disease, Alzheimer's Disease and osteoarthritis.

The present invention provides for compounds of formula I, pharmaceutical compositions employing such compounds, and for methods of using such compounds. In particular, the present invention provides a pharmaceutical composition comprising a therapeutically effective amount of a compound of formula I alone or in combination with a pharmaceutically acceptable carrier.

Further, in accordance with the present invention, a method is provided for preventing, inhibiting, or treating the progression or onset of diseases or disorders associated with the activity of the enzyme 11-beta-hydroxysteroid dehydrogenase type I, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting, or treating the diseases as defined above and hereinafter, wherein a therapeutically effective amount of a combination of a compound of formula I and another compound of formula I and/or at least one other type of therapeutic agent, is administered to a mammalian, i.e., human, patient in need of treatment.

DESCRIPTION OF THE INVENTION

In accordance with the present invention, pharmaceutically-active compounds of formula I:

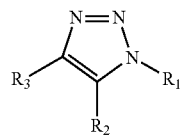

(I)

enantiomers, diastereomers, or salts thereof wherein:

$R_1$ is aryl or bicycloalkyl, both of which may be optionally substituted with one or more $R_{1a}$'s;

$R_{1a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —C(=O)OH, —C(=O)$OR_{14}$, —$OCF_3$, —$OR_{10}$, —OH, —$OCF_3$, —SH, —$SR_{14}$, —C(=O)$NR_{14}R_{14}$, —$NR_{14}R_{14}$, —C(=O)$R_{14}$, —$NR_{14}$C(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$NR_{14}$C(=O)$OR_{10}$, —OC(=O)$NR_{14}R_{14}$, —$NR_{14}$C(=O)$NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_2$ is unsubstituted $C_{1-4}$ alkyl or cycloalkyl;

$R_3$ is aryl or bicycloalkyl, both of which may be optionally substituted with one or more $R_{3a}$'s;

$R_{3a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{14}$, —$OCF_3$, —$OR_{10}$, —OH, —$OCF_3$, —SH, —$SR_{14}$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{10}$, —$S(O)_2NR_{14}$C(=O)$OR_{10}$, —$S(O)_2NR_{14}$C(=O)$NR_{14}R_{14}$, —C(=O)$NR_{14}S(O)_2R_{14}$, —C(=O)$R_{14}$, —$NR_{14}$C(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$OS(O)_2R_{14}$, —$NR_{14}$C(=O)$OR_{10}$, —$NR_{14}S(O_2)R_8$, —OC(=O)$NR_{14}R_{14}$, —$NR_{14}$C(=O)$NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_8$, at each occurrence, is independently alkyl, aryl or heterocyclyl;

$R_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —$OCF_3$, —$OR_{14}$, —OH, —SH, —$SR_{14}$, —C(=O)$NR_{14}R_{14}$, —$NR_{14}R_{14}$, —$S(O)_2NR_{14}R_{14}$, —$NR_{14}S(O)_2CF_3$, —C(=O)$NR_{14}S(O)_2R_{14}$, —$S(O)_2NR_{14}$C(=O)$OR_{14}$, —$S(O)_2NR_{14}$C(=O)$NR_{14}R_{14}$, —C(=O)$NR_{14}S(O)_2CF_3$, —C(=O)$R_{14}$, —$NR_{14}$C(=O)$R_{14}$, —OC(=O)$R_{14}$, —C(=$NR_{14}$)$NR_{14}R_{14}$, —NHC(=$NR_{14}$)$NR_{14}R_{14}$, —S(=O)$R_{14}$, —$S(O)_2R_{14}$, —$NR_{14}$C(=O)$OR_8$, —$NR_{14}S(O_2)R_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —$NO_2$, —C(=O)OH, —C(=O)$OR_{15}$, —$OCF_3$, —$OR_{15}$, —OH, —SH, —$SR_{15}$, —C(=O)$NR_{15}R_{15}$, —$NR_{15}R_{15}$, —$S(O)_2NR_{15}R_{15}$, —$NR_{15}S(O)_2CF_3$, —C(=O)$NR_{15}S(O)_2R_{15}$, —$S(O)_2NR_{15}$C(=O)$OR_{15}$, —$S(O)_2NR_{15}$C(=O)$NR_{15}R_{15}$, —C(=O)$NR_{15}S(O)_2CF_3$, —C(=O)$R_{15}$, —$NR_{15}$C(=O)$R_{15}$, —OC(=O)$R_{15}$, —C(=$NR_{15}$)$NR_{15}R_{15}$, —NHC(=$NR_{15}$)$NR_{15}R_{15}$, —S(=O)$R_{15}$, —$S(O)_2R_{15}$, —$NR_{15}$C(=O)$OR_8$, —$NR_{15}S(O_2)R_8$ or arylalkyl; and $R_{15}$, at each occurrence, is independently selected from hydrogen, alkyl, cycloalkyl, aryl or arylalkyl.

In another embodiment, compounds are those in which $R_1$ is aryl, which may be optionally substituted with one or more $R_{1a}$'s.

In another embodiment, compounds are those in which $R_1$ is a monocyclic aryl, which may be optionally substituted with one or more $R_{1a}$'s.

In another embodiment, compounds are those in which $R_3$ is bicycloalkyl, which may be optionally substituted with one or more $R_{3a}$'s.

In yet another embodiment, compounds are those in which $R_1$ is a monocyclic aryl, which may be optionally substituted with one or more $R_{1a}$'s and $R_3$ is a [2,2,2]bicycloalkyl, which may be optionally substituted with one or more $R_{3a}$'s.

In another embodiment, compounds are those in which $R_1$ is bicycloalkyl, which may be optionally substituted with one or more $R_{1a}$'s.

In still yet another embodiment, compounds are those in which $R_3$ is aryl, which may be optionally substituted with one or more $R_{3a}$'s.

In one embodiment, compounds are those in which $R_3$ is a monocyclic aryl, which may be optionally substituted with one or more $R_{3a}$'s.

In still yet another embodiment, compounds are those in which $R_1$ is bicycloalkyl, which may be optionally substituted with one or more $R_{1a}$'s and $R_3$ is a monocyclic aryl, which may be optionally substituted with one or more $R_{3a}$'s.

In still yet another embodiment, compounds are those in which: $R_1$ is aryl or bicycloalkyl, both of which may be optionally substituted with one or more $R_{1a}$'s;

$R_{1a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —C(=O)OH, —C(=O)O$R_{14}$, —OCF$_3$, —O$R_{10}$, —OH, —OCF$_3$, —SH, —S$R_{14}$, —C(=O)N$R_{14}R_{14}$, —N$R_{14}R_{14}$, —C(=O)$R_{14}$, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —N$R_{14}$C(=O)O$R_{10}$, —OC(=O)N$R_{14}R_{14}$, —N$R_{14}$C(=O)N$R_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_2$ is unsubstituted $C_{1-3}$ alkyl or cycloalkyl;

$R_3$ is aryl or bicycloalkyl, both of which may be optionally substituted with one or more $R_{3a}$'s;

$R_{3a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)O$R_{14}$, —OCF$_3$, —O$R_{10}$, —OH, —OCF$_3$, —SH, —S$R_{14}$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_{10}$, —S(O)$_2$N$R_{14}$C(=O)O$R_{10}$, —S(O)$_2$N$R_{14}$C(=O)N$R_{14}R_{14}$, —C(=O)N$R_{14}$S(O)$_2R_{14}$, —C(=O)$R_{14}$, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2R_{14}$, —OS(O)$_2R_{14}$, —N$R_{14}$C(=O)O$R_{10}$, —N$R_{14}$S(O$_2$)$R_8$, —OC(=O)N$R_{14}R_{14}$, —N$R_{14}$C(=O)N$R_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_8$, at each occurrence, is independently alkyl, aryl or heterocyclyl;

$R_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —OCF$_3$, —O$R_{14}$, —OH, —SH, —S$R_{14}$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_{14}$, —S(O)$_2$N$R_{14}$C(=O)O$R_{14}$, —S(O)$_2$N$R_{14}$C(=O)N$R_{14}R_{14}$, —C(=O)N$R_{14}$S(O)$_2$CF$_3$, —C(=O)$R_{14}$, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2R_{14}$, —N$R_{14}$C(=O)O$R_8$, —N$R_{14}$S(O$_2$)$R_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —$NO_2$, —C(=O)OH, —C(=O)O$R_{15}$, —OCF$_3$, —O$R_{15}$, —OH, —SH, —S$R_{15}$, —C(=O)N$R_{15}R_{15}$, —N$R_{15}R_{15}$, —S(O)$_2$N$R_{15}R_{15}$, —N$R_{15}$S(O)$_2$CF$_3$, —C(=O)N$R_{15}$S(O)$_2R_{15}$, —S(O)$_2$N$R_{15}$C(=O)O$R_{15}$, —S(O)$_2$N$R_{15}$C(=O)N$R_{15}R_{15}$, —C(=O)N$R_{15}$S(O)$_2$CF$_3$, —C(=O)$R_{15}$, —N$R_{15}$C(=O)$R_{15}$, —OC(=O)$R_{15}$, —C(=N$R_{15}$)N$R_{15}R_{15}$, —NHC(=N$R_{15}$)N$R_{15}R_{15}$, —S(=O)$R_{15}$, —S(O)$_2R_{15}$, —N$R_{15}$C(=O)O$R_8$, —N$R_{15}$S(O$_2$)$R_8$ or arylalkyl; and $R_{15}$, at each occurrence, is independently selected from hydrogen, alkyl, cycloalkyl, aryl or arylalkyl.

In another embodiment, compounds are those compounds in which: $R_1$ is a monocyclic aryl or bicycloalkyl, both which may be optionally substituted with one or more $R_{1a}$'s;

$R_{1a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —C(=O)OH, —C(=O)O$R_{14}$, —OCF$_3$, —O$R_{10}$, —OH, —OCF$_3$, —SH, —S$R_{14}$, —C(=O)N$R_{14}R_{14}$, —N$R_{14}R_{14}$, —C(=O)$R_{14}$, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —N$R_{14}$C(=O)O$R_{10}$, —OC(=O)N$R_{14}R_{14}$, —N$R_{14}$C(=O)N$R_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_2$ is unsubstituted $C_{1-3}$ alkyl or cycloalkyl;

$R_3$ is aryl or bicycloalkyl, both of which may be optionally substituted with one or more $R_{3a}$'s;

$R_{3a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)O$R_{14}$, —OCF$_3$, —O$R_{10}$, —OH, —OCF$_3$, —SH, —S$R_{14}$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_{10}$, —S(O)$_2$N$R_{14}$C(=O)O$R_{10}$, —S(O)$_2$N$R_{14}$C(=O)N$R_{14}R_{14}$, —C(=O)N$R_{14}$S(O)$_2R_{14}$, —C(=O)$R_{14}$, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2R_{14}$, —OS(O)$_2R_{14}$, —N$R_{14}$C(=O)O$R_{10}$, —N$R_{14}$S(O$_2$)$R_8$, —OC(=O)N$R_{14}R_{14}$, —N$R_{14}$C(=O)N$R_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_8$, at each occurrence, is independently alkyl, aryl or heterocyclyl;

$R_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —OCF$_3$, —O$R_{14}$, —OH, —SH, —S$R_{14}$, —C(=O)N$R_{14}R_{14}$, —N$R_{14}R_{14}$, —S(O)$_2$N$R_{14}R_{14}$, —N$R_{14}$S(O)$_2$CF$_3$, —C(=O)N$R_{14}$S(O)$_2R_{14}$, —S(O)$_2$N$R_{14}$C(=O)O$R_{14}$, —S(O)$_2$N$R_{14}$C(=O)N$R_{14}R_{14}$, —C(=O)N$R_{14}$S(O)$_2$CF$_3$, —C(=O)$R_{14}$, —N$R_{14}$C(=O)$R_{14}$, —OC(=O)$R_{14}$, —C(=N$R_{14}$)N$R_{14}R_{14}$, —NHC(=N$R_{14}$)N$R_{14}R_{14}$, —S(=O)$R_{14}$, —S(O)$_2R_{14}$, —N$R_{14}$C(=O)O$R_8$, —N$R_{14}$S(O$_2$)$R_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —$NO_2$, —C(=O)OH, —C(=O)O$R_{15}$, —OCF$_3$, —O$R_{15}$, —OH, —SH, —S$R_{15}$, —C(=O)N$R_{15}R_{15}$, —N$R_{15}R_{15}$, —S(O)$_2$N$R_{15}R_{15}$, —N$R_{15}$S(O)$_2$CF$_3$, —C(=O)N$R_{15}$S(O)$_2R_{15}$, —S(O)$_2$N$R_{15}$C(=O)O$R_{15}$, —S(O)$_2$N$R_{15}$C(=O)N$R_{15}R_{15}$, —C(=O)N$R_{15}$S(O)$_2$CF$_3$, —C(=O)$R_{15}$, —N$R_{15}$C(=O)$R_{15}$, —OC(=O)$R_{15}$, —C(=N$R_{15}$)N$R_{15}R_{15}$, —NHC (=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

In another embodiment, compounds are those compounds in which:

R$_1$ is a monocyclic aryl or bicycloalkyl, both of which may be optionally substituted with one or more R$_{1a}$'s;

R$_{1a}$, at each occurrence, is independently selected from alkyl, haloalkyl, aryl, alkynyl, cycloalkyl, cycloalkylalkyl, heterocyclyl, heterocyclylalkyl, halo, —NH$_2$, —OCF$_3$, —OR$_{10}$, —OCF$_3$, —C(=O)NR$_{14}$R$_{14}$, —NR$_{14}$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —NR$_{14}$C(=O)OR$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_2$ is unsubstituted C$_{1-3}$ alkyl or cycloalkyl;

R$_3$ is aryl or bicycloalkyl, both of which may be optionally substituted with one or more R$_{3a}$'s;

R$_{3a}$, at each occurrence, is independently selected from alkyl, haloalkyl, aryl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_8$, at each occurrence, is independently alkyl, aryl or heterocyclyl;

R$_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —C(=NR$_{15}$)NR$_{15}$R$_{15}$, —NHC(=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

In another embodiment, compounds are those compounds in which:

R$_1$ is a monocyclic aryl or bicycloalkyl, both of which may be optionally substituted with one or more R$_{1a}$'s;

R$_{1a}$, at each occurrence, is independently selected from alkyl, haloalkyl, aryl, alkynyl, cycloalkyl, cycloalkylalkyl, heterocyclyl, heterocyclylalkyl, halo, —NH$_2$, —OCF$_3$, —OR$_{10}$, —OCF$_3$, —C(=O)NR$_{14}$R$_{14}$, —NR$_{14}$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —NR$_{14}$C(=O)OR$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_2$ is C$_{1-3}$ alkyl;

R$_3$ is aryl or bicycloalkyl, both of which may be optionally substituted with one or more R$_{3a}$'s;

R$_{3a}$, at each occurrence, is independently selected from alkyl, haloalkyl, aryl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_8$, at each occurrence, is independently alkyl, aryl or heterocyclyl;

R$_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O) R$_{15}$, —OC(=O)R$_{15}$, —C(=NR$_{15}$)NR$_{15}$R$_{15}$, —NHC(=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

In another embodiment, compounds are those compounds in which:

R$_1$ is phenyl or bicycloalkyl, both of which may be optionally substituted with one or more R$_{1a}$'s;

R$_{1a}$, at each occurrence, is independently selected from alkyl, haloalkyl, aryl, alkynyl, cycloalkyl, cycloalkylalkyl, heterocyclyl, heterocyclylalkyl, halo, —NH$_2$, —OCF$_3$, —OR$_{10}$, —OCF$_3$, —C(=O)NR$_{14}$R$_{14}$, —NR$_{14}$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —NR$_{14}$C(=O)OR$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_2$ is C$_{1-3}$ alkyl;

R$_3$ is aryl or bicycloalkyl, both of which may be optionally substituted with one or more R$_{3a}$'s;

R$_{3a}$, at each occurrence, is independently selected from alkyl, haloalkyl, aryl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_8$, at each occurrence, is independently alkyl, aryl or heterocyclyl;

R$_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —C(=NR$_{15}$)NR$_{15}$R$_{15}$, —NHC(=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

In another embodiment, compounds are those compounds in which:

R$_1$ is phenyl or bicycloalkyl, both of which may be optionally substituted with one or more R$_{1a}$'s;

R$_{1a}$, at each occurrence, is independently selected from alkyl, haloalkyl, aryl, alkynyl, cycloalkyl, cycloalkylalkyl, heterocyclyl, heterocyclylalkyl, halo, —NH$_2$, —OCF$_3$, —OR$_{10}$, —OCF$_3$, —C(=O)NR$_{14}$R$_{14}$, —NR$_{14}$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —NR$_{14}$C(=O)OR$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_2$ is methyl;

R$_3$ is phenyl or bicycloalkyl, both of which may be optionally substituted with one or more R$_{3a}$'s;

R$_{3a}$, at each occurrence, is independently selected from alkyl, haloalkyl, aryl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_8$, at each occurrence, is independently alkyl, aryl or heterocyclyl;

R$_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —OCF$_3$, —OR$_{14}$, —OH, —SH, —SR$_{14}$, —C(=O) NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —C(=NR$_{15}$)NR$_{15}$R$_{15}$, —NHC(=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

In another embodiment, pharmaceutically-active compounds of the present invention are selected from the compounds exemplified in the examples.

In another embodiment, the present invention relates to pharmaceutical compositions comprised of a therapeutically effective amount of a compound of the present invention, alone or, optionally, in combination with a pharmaceutically acceptable carrier and/or one or more other agent(s).

In another embodiment, the present invention relates to methods of inhibiting the activity of the enzyme 11-beta-hydroxysteroid dehydrogenase type I comprising administering to a mammalian patient, for example, a human patient, in need thereof a therapeutically effective amount of a compound of the present invention, alone, or optionally, in combination with another compound of the present invention and/or at least one other type of therapeutic agent.

In another embodiment, the present invention relates to a method for preventing, inhibiting, or treating the progression or onset of diseases or disorders associated with the activity of the enzyme 11-beta-hydroxysteroid dehydrogenase type I comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis, acute coronary syndrome, myocardial infarction, angina pectoris, peripheral vascular disease, intermittent claudication, abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma, rheumatoid arthritis, Cushing's Disease, Alzheimer's Disease and osteoarthritis.

In another embodiment, the present invention relates to a method for preventing, inhibiting, or treating the progression or onset of diabetes, hyperglycemia, obesity, dislipidemia, hypertension, cognitive impairment, rheumatoid arthritis, osteoarthritis, glaucoma, Cushing's Disease and Metabolic Syndrome comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In still another embodiment, the present invention relates to a method for preventing, inhibiting, or treating the progression or onset of diabetes, comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In yet still another embodiment, the present invention relates to a method for preventing, inhibiting, or treating the progression or onset of hyperglycemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of obesity comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In one embodiment, the present invention relates to a method for preventing, inhibiting, or treating the progression or onset of dislipidemia comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of hypertension comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of cognitive impairment comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of rheumatoid arthritis comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of osteoarthritis comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of Metabolic Syndrome comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of glaucoma comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

In another embodiment, the present invention relates to a method for preventing, inhibiting, or treating the progression or onset of Cushing's Disease comprising administering to a mammalian patient, for example, a human patient, in need of prevention, inhibition, or treatment a therapeutically effective amount of a compound of the present invention, alone, or, optionally, in combination with another compound of the present invention and/or at least one other type of therapeutic agent.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young et al., *Antimicrobial Agents and Chemotherapy*, 2602-2605 (1995).

To the extent that compounds of the formula I, and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

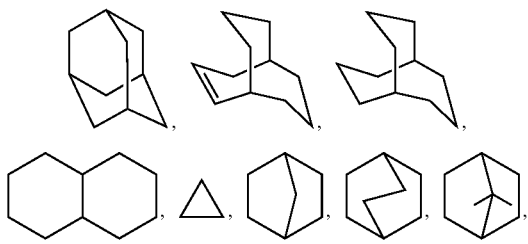

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $—C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

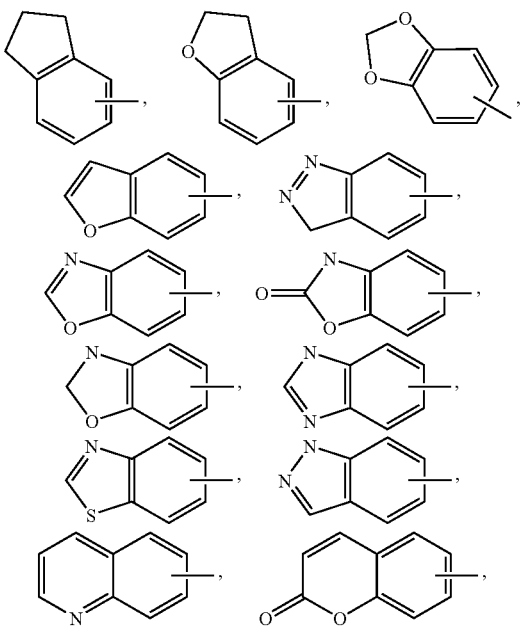

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl", "heterocyclic system" or "heterocyclic ring" is intended to mean a stable 3- to 14-membered monocyclic, bicyclic or tricyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds. Ch. 5, pp. 113-191 (Harwood Academic Publishers, 1991); and d) *Hydrolysis in Drug and Prodrug Metabolism*, Bernard Testa and Joachim M. Mayer (Wiley-VCH, 2003).

Said references are incorporated herein by reference.

In addition, compounds of the formula I are, subsequent to their preparation, preferably isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of formula I can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization. In addition, the compounds of formula I may exist in tautomeric form. Such tautomeric forms of the formula I are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

SYNTHESIS

Compounds of the present invention may be prepared as shown in the following reaction schemes and description thereof, as well as relevant literature procedures that may be used by one skilled in the art. Exemplary reagents and procedures for these reactions appear hereinafter and in the working Examples.

SCHEME I

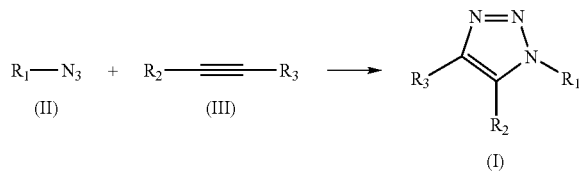

Scheme I describes a method for preparing compounds of formula I from a 1,3-dipolar cycloaddition reaction. Both azide II and alkyne III can be obtained commercially, prepared by methods known in the literature or by other methods known to one skilled in the art. For Example, when $R_1$ is alkyl or cycloalkyl, the azide II can be prepared from the reaction of the appropriate alkyl or cycloalkyl halides with sodium azide or trimethylsilyl azide and TBAF. When $R_1$ is aryl or heteroaryl, the azide II can be prepared from the reaction of aryl halides and sodium azide in the presence of copper (I) iodide catalyst (ref. Q. Cai et al. *Synlett,* 496-499 (2005); J. Anderson et al. *Synlett,* 2209-2213 (2005)).

SCHEME II

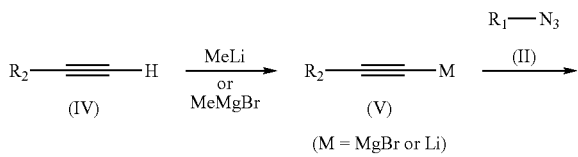

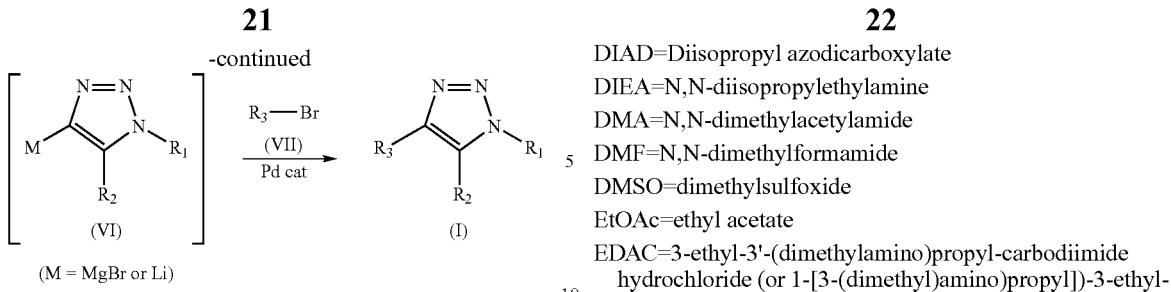

(M = MgBr or Li)

Scheme II describes an alternative method for preparing compounds of formula I from a 1,3-dipolar cycloaddition reaction when $R_3$ is an aryl or heteroaryl group. The alkyne IV can be deprotonated with a strong base such as methyllithium or methylmagnesium bromide to give the intermediate V which was allowed to react with azide II to give an intermediate VI. Negishi type coupling reaction of VI with VII can be accomplished with addition of zinc chloride and an appropriate catalyst and ligand. (ref A. Akao et al. *Synlett*, 31-36 (2007)).

EXAMPLES

The following working Examples serve to better illustrate, but not limit, some of the preferred embodiments of the present invention.

General

The term HPLC refers to a Shimadzu high performance liquid chromatography with one of following methods:
Analytical HPLC (Method A): YMC or Phenomenex C18 5 micron 4.6×50 mm column using a 4 minute gradient of 0-100% solvent B [90% MeOH:10% $H_2O$:0.2% $H_3PO_4$] and 100-0% solvent A [10% MeOH:90% $H_2O$:0.2% $H_3PO_4$] with 4 mL/min flow rate and a 1 min. hold, an ultra violet (UV) detector set at 220 nm.
Prep HPLC (Method B): Refers to an automated Shimadzu HPLC system using a mixture of solvent A (10% MeOH/90% $H_2O$/0.2% TFA) and solvent B (90% MeOH/10% $H_2O$/0.2% TFA). The preparative columns were packed with YMC or Phenomenex ODS C18 5 micron resin or equivalent.
Prep HPLC (Method C): Refers to an automated Shimadzu HPLC system using a mixture of solvent A (10% $CH_3CN$/90% $H_2O$/0.2% TFA) and solvent B (90% $CH_3CN$/10% $H_2O$/0.2% TFA). The preparative columns were packed with YMC or Phenomenex ODS C18 5 micron resin or equivalent.

ABBREVIATIONS

The following abbreviations are employed in the Examples and elsewhere herein:
Ph=phenyl
Bn=benzyl
Bu=iso-butyl
Me=methyl
Et=ethyl
Pr=propyl
Bu=butyl
AIBN=2,2'-Azobisisobutyronitrile
Boc or BOC=tert-butoxycarbonyl
Cbz=carbobenzyloxy or carbobenzoxy or benzyloxycarbonyl
CDI=1,1'-carbonyldiimidazole
DCM=dichloromethane
DEAD=Diethyl azodicarboxylate
DIAD=Diisopropyl azodicarboxylate
DIEA=N,N-diisopropylethylamine
DMA=N,N-dimethylacetylamide
DMF=N,N-dimethylformamide
DMSO=dimethylsulfoxide
EtOAc=ethyl acetate
EDAC=3-ethyl-3'-(dimethylamino)propyl-carbodiimide hydrochloride (or 1-[3-(dimethyl)amino)propyl])-3-ethyl-carbodiimide hydrochloride)
FMOC=fluorenylmethoxycarbonyl
HOAc or AcOH=acetic acid
HOAT=1-hydroxy-7-azabenzotriazole
HOBT=1-hydroxybenzotriazole
LAH=lithium aluminum hydride
mCPBA=3-Chloroperoxybenzoic acid
NMM=N-methyl morpholine
NBS=N-Bromosuccinimide
n-BuLi=n-butyllithium
Oxone®=Monopersulfate
Pd2(dba)3=tris(dibenzylideneacetone)dipalladium
Pd/C=palladium on carbon
$PtO_2$=platinum oxide
PyBOP reagent=benzotriazol-1-yloxy-tripyrrolidino phosphonium hexafluorophosphate
$SOCl_2$=Thionyl chloride
TBAF=tetrabutylammonium fluoride
TBS=tert-Butyldimethylsilyl
TMS=trimethylsilyl
TEA=triethylamine
TFA=trifluoroacetic acid
THF=tetrahydrofuran
equiv=equivalent(s)
min=minute(s)
h or hr=hour(s)
L=liter
mL=milliliter
µL=microliter
g=gram(s)
mg=milligram(s)
mol=mole(s)
mmol=millimole(s)
meq=milliequivalent
RT=room temperature
sat or sat'd=saturated
aq.=aqueous
TLC=thin layer chromatography
HPLC=high performance liquid chromatography
HPLC $R_t$=HPLC retention time
LC/MS=high performance liquid chromatography/mass spectrometry
MS or Mass Spec=mass spectrometry
NMR=nuclear magnetic resonance
mp=melting point

Example 1

1-(1-Adamantyl)-4-phenyl-5-ethyl-1H-1,2,3-triazole

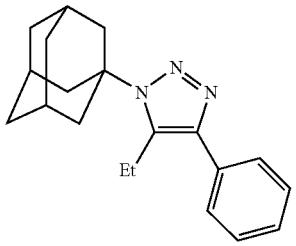

To a solution of azidoadamantane (100 mg, 0.56 mmol) in dioxane (1 mL) was added but-1-ynylbenzene (367 mg, 2.8 mmol) at room temperature. Upon completion of addition, the reaction was stirred under nitrogen at 100° C. for 12 hr, followed by 160° C. for 30 min under a microwave reactor. After this time, two drops of 1-butyl-3-methylimidazolium hexafluorophosphate was added as an ionic liquid to facilitate microwave energy absorption. The crude product was concentrated to yield a residue. The residue was purified by reverse phase preparative HPLC (Method C) to provide Example 1 (8.5 mg, 4% yield) as a pale yellow solid as the TFA salt. HPLC 95% purity (Method A); LC/MS=308 (M+H)+; 1HNMR (MeOH-d4) δ 7.57-7.61 (m, 2H), 7.47 (t, J=6.0 Hz, 2H), 7.38-7.43 (m, 1H), 3.16 (q, J=7.7 Hz, 2H), 2.45 (d, J=3.3 Hz, 6H), 2.28 (br s, 3H), 1.87 (br s, 6H), 1.51 (t, J=7.7 Hz, 3H).

Example 2

1-(1-Adamantyl)-4-(2-chlorophenyl)-5-methyl-1H-1,2,3-triazole

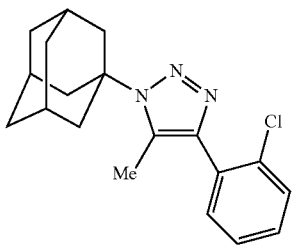

To azidoadamantane (177 mg, 1 mmol) was added a prop-1-ynylmagnesium bromide (2.2 mL, 0.5 M, 1.1 mmol) THF solution at room temperature. Upon completion of addition, the reaction mixture was stirred under nitrogen at room temperature for 2 hr. At the conclusion of this period, zinc(II) chloride (163 mg, 1.2 mmol) was added to the mixture, and the stirring was continued for another hour at room temperature. After this time, 1-bromo-2-chlorobenzene (210 mg, 1.1 mmol), 4,5-bis(diphenylphosphino)-9,9-dimethylxanthene (28.9 mg, 0.05 mmol) and Pd$_2$(dba)$_3$ (18.3 mg, 0.02 mmol) were added. The resulting mixture was heated at 65° C. for 12 hr, and then cooled to room temperature. Once at the prescribed temperature, the reaction mixture was concentrated, diluted with EtOAc, washed with brine, dried over Na$_2$SO$_4$, and concentrated to yield the crude product. The crude product was purified by silica gel chromatography, eluting with 0-10% EtOAc in hexanes, to provide Example 2 (9 mg, 3% yield) as a pale yellow solid. HPLC 98% purity (Method A); LC/MS=328/330 (M+H)+; 1HNMR (MeOH-d4) δ 7.57-7.59 (m, 1H), 7.43-7.48 (m, 2H), 7.38-7.41 (m, 1H), 2.64 (s, 3H), 2.44 (d, J=3.3 Hz, 6H), 2.28 (br s, 3H), 1.81 (br s, 6H).

Example 3

3-(4-Fluorophenyl)-5-(4-(5-methyl-1-(2-(trifluoromethyl)phenyl)-1H-1,2,3-triazol-4-yl)bicyclo[2.2.2]octan-1-yl)-1,2,4-oxadiazole

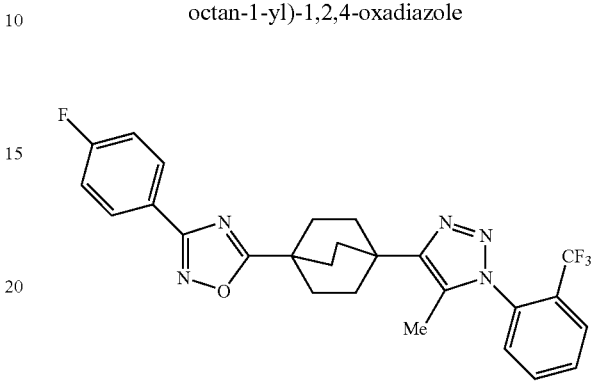

Compound 3A: 4-(Methoxycarbonyl)bicyclo[2.2.2]octane-1-carboxylic acid

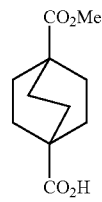

To a solution of dimethyl bicyclo[2.2.2]octane-1,4-dicarboxylate (4.3 g, 19 mmol, see J. Roberts et al., *J. Am. Chem. Soc.*, 75:637-640 (1953)) in methanol (15 mL) was added lithium hydroxide (5 mL, 4 M, 20 mmol) at room temperature. Upon completion of addition, the reaction was stirred at 65° C. for 6 hr. After this time, the reaction mixture was concentrated, and EtOAc and water were added. The pH of the resulting mixture was adjusted to 1 with ca. 1.7 mL of conc. HCl. The resulting mixture was extracted with EtOAc. The EtOAc layers were combined, dried over Na$_2$SO$_4$, and then concentrated to give compound 3A (3.55 g, 88% yield) as a white solid. $^1$H NMR (MeOH-d4) δ 3.51 (s, 3H), 1.69 (s, 12H).

Compound 3B: Methyl 4-(3-(4-fluorophenyl)-1,2,4-oxadiazol-5-yl)bicyclo[2.2.2]-octane-1-carboxylate

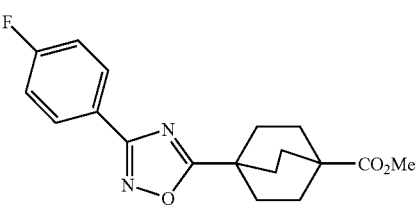

To compound 3A (3.4 g, 16 mmol) in CH$_2$Cl$_2$ (60 mL) was added CDI (3.9 g, 24 mmol) at room temperature. The resulting mixture was stirred for 1 hr, and then 4-fluoro-N'-hydroxybenzimidamide (4.94 g, 32.0 mmol) was added. Upon completion of addition, the stirring was continued at room temperature for 8 hr. After this time, the reaction mixture was concentrated, and toluene (40 mL) was added. The resulting mixture was heated to reflux where it stirred for 14 hr. At the conclusion of this period, the reaction mixture was diluted with 100 mL of EtOAc, washed with brine solution once, dried over $Na_2SO_4$, and then concentrated to give the crude product. The crude product was purified by silica gel chromatography, eluting with 0-20% EtOAc in hexanes, to provide compound 3B (4.3 g, 88% purity, 72% yield) as a white solid. LC/MS=331 (M+H)+; $^1$H NMR (CDCl3) δ 8.02-8.07 (m, 2H), 7.13 (d, J=8.8 Hz, 2H), 3.68 (s, 3H), 2.02-2.09 (m, 6H), 1.90-1.98 (m, 6H).

Compound 3C: (4-(3-(4-Fluorophenyl)-1,2,4-oxadiazol-5-yl)bicyclo[2.2.2]octan-1-yl)methanol

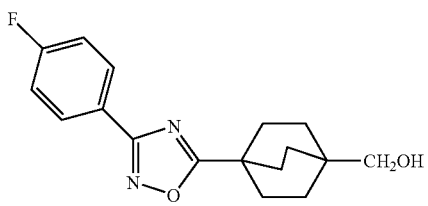

To a solution of compound 3B (4.3 g, 88% purity, 11.4 mmol) in $CH_2Cl_2$ (50 mL) was added diisobutylaluminum hydride (25.2 mL, 1.0 M, 25.2 mmol) at −78° C. Upon completion of addition, the reaction mixture was warmed to 0° C. where it stirred for 1 hr. After this time, the reaction mixture was slowly quenched with water, and then diluted with $CH_2Cl_2$. The resulting solid was removed by filtration, and the organic layer was washed with water, dried over $Na_2SO_4$, and then concentrated to give the crude product. The crude product was purified by silica gel chromatography, eluting with 10-50% EtOAc in hexanes, to provide compound 3C (3.0 g, 87% yield) as a white solid. HPLC 98% purity (Method A), LC/MS=303 (M+H)+, $^1$H NMR (CDCl3) δ 8.02-8.08 (m, 2H), 7.13 (d, J=8.4 Hz, 2H), 3.40 (s, 2H), 2.00-2.07 (m, 6H), 1.50-1.60 (m, 6H).

Compound 3D: 4-(3-(4-Fluorophenyl)-1,2,4-oxadiazol-5-yl)bicyclo[2.2.2]octane-1-carbaldehyde

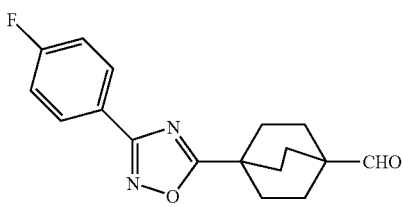

To a solution of compound 3C (3.0 g, 9.9 mmol) in $CH_2Cl_2$ (30 mL) was added Dess-Martin Periodinane (4.21 g, 9.9 mmol) at room temperature. Upon completion of addition, the reaction mixture was stirred at room temperature for 3 hr. After this time, the reaction mixture was slowly quenched with 10% aqueous $Na_2SO_3$, and then diluted with $CH_2Cl_2$. The resulting solid was removed by filtration, and the organic layer was washed with water, dried over $Na_2SO_4$, and then concentrated to give the crude product. The crude product was purified by silica gel chromatography, eluting with 10-20% EtOAc in hexanes, to provide compound 3D (1.8 g, 60% yield) as a white solid. HPLC purity 98% (Method A); LC/MS=333 (M+MeOH+H)+; $^1$H NMR (CDCl3) δ 9.50 (s, 1H), 8.02-8.08 (m, 2H), 7.14 (d, J=8.4 Hz, 2H), 2.05-2.12 (m, 6H), 1.76-1.83 (m, 6H).

Compound 3E: 5-(4-(2,2-Dibromovinyl)bicyclo [2.2.2]octan-1-yl)-3-(4-fluorophenyl)-1,2,4-oxadiazole

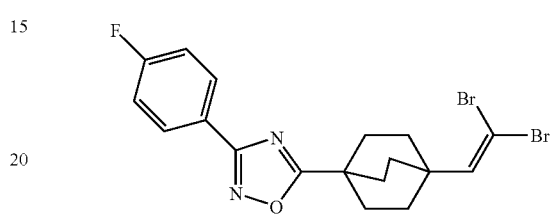

To a solution of carbon tetrabromide (2.98 g, 9.0 mmol) in $CH_2Cl_2$ (40 mL) was slowly added triphenylphosphine (4.72 g, 18.0 mmol) at room temperature. The resulting dark brown mixture was stirred at room temperature for 30 min and then a solution of compound 3D (1.8 g, 6.0 mmol) in $CH_2Cl_2$ (20 mL) was slowly added at room temperature. Upon completion of addition, the reaction mixture was stirred for another 30 min at room temperature and then diluted with $CH_2Cl_2$ and water. The $CH_2Cl_2$ layer was dried over $Na_2SO_4$, and the concentrated to yield a residue. The residue was taken up in EtOAc (100 mL). The resulting solid ($Ph_3PO$) was removed by filtration, and the EtOAc filtrate was concentrated to yield the crude product. The crude product was purified by silica gel chromatography, eluting with 0-20% EtOAc in hexanes, to provided compound 3E (1.55 g, 57% yield) as a white solid. HPLC 98% purity (Method A); LC/MS=455/457/459 (M+H)+; $^1$H NMR (CDCl3) δ 8.01-8.07 (m, 2H), 7.14 (d, J=8.4 Hz, 2H), 6.47 (s, 1H), 2.02-2.07 (m, 6H), 1.93-1.98 (m, 6H).

Compound 3F: 3-(4-Fluorophenyl)-5-(4-(prop-1-ynyl)bicyclo[2.2.2]octan-1-yl)-1,2,4-oxadiazole

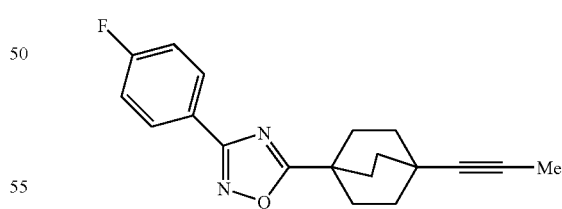

To a solution of compound 3E (1.5 g, 3.29 mmol) in THF (30 mL) was slowly added n-BuLi (4.3 mL, 1.6 M, 6.9 mmol) at −78° C. Upon completion of addition, the reaction mixture was stirred at −78° C. for 60 min. After this time, iodomethane (0.617 mL, 9.9 mmol) was slowly added at −78° C. The resulting mixture was stirred for another 30 min at −78° C. and then quenched with water. The resulting solution was concentrated to yield a residue. The residue was dissolved in EtOAc, washed with brine, dried over $Na_2SO_4$, and then concentrated to yield the crude product. The crude product was purified by silica gel chromatography, eluting with 0-20% EtOAc in hexanes, to provide compound 3F (715 mg, 70% yield) as a white solid. HPLC 95% purity, Rt 4.443 min (Method A); LC/MS=311 (M+H)+; $^1$H NMR (CDCl3) δ 8.01-8.07 (m, 2H), 7.14 (d, J=8.4 Hz, 2H), 1.98-2.04 (m, 6H), 1.82-1.88 (m, 6H), 1.78 (s, 3H).

Compound 3G: Azido-2-(trifluoromethyl)benzene

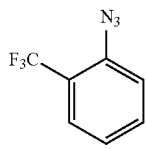

To a solution of 1-iodo-2-(trifluoromethyl)benzene (5.44 g, 20.0 mmol) in DMSO (25 mL) was added (1R,2R)—N1, N2-dimethylcyclohexane-1,2-diamine (0.427 g, 3.0 mmol), copper(I) iodide (0.381 g, 2.0 mmol), sodium ascorbate (0.198 g, 1.0 mmol), and sodium azide (2.60 g, 40.0 mmol) in water (5 mL) at room temperature. Upon completion of addition, the reaction mixture was warmed to 80° C. where it stirred for 18 hr. After this time, the reaction mixture was diluted with 300 mL of a EtOAc/hexanes (1:1) solution, washed with brine (4×), dried over Na$_2$SO$_4$, and then concentrated to give the crude product. The crude product was purified by silica gel chromatography, eluting with 100% hexanes, to provide compound 3G (1.8 g, 48% yield) as a pale yellow liquid. $^1$H NMR (CDCl3) δ 7.63 (d, J=7.7 Hz, 1H), 7.57 (t, J=7.2 Hz, 1H), 7.30 (d, J=8.3 Hz, 1H), 7.22 (d, J=7.7 Hz, 1H).

Example 3

To a mixture of compound 3F (100 mg, 0.32 mmol) and compound 3G (121 mg, 0.64 mmol) in toluene (2 mL) was added copper(I) chloride (3.19 mg, 0.032 mmol) at room temperature. Upon completion of addition, the reaction mixture was warmed to 120° C. where it stirred for 48 hr. After this time, the reaction mixture was cooled to the room temperature. Once at the prescribed temperature, the reaction mixture was diluted with EtOAc, washed with brine, dried over Na$_2$SO$_4$, and then concentrated to yield a residue. The residue was purified by reverse phase preparative HPLC (Method B) to provide the crude product. The crude product was further purified by silica gel chromatography, eluting with 10-30% EtOAc in hexanes, to provide Example 3 (19 mg, 12% yield) as an off-white solid. HPLC 98% purity, Rt 4.138 min (Method A); LC/MS=498 (M+H)+; $^1$H NMR (MeOH-d4) δ 8.06-8.12 (m, 2H), 7.97-8.01 (m, 1H), 7.82-7.92 (m, 2H), 7.54 (d, J=7.1 Hz, 2H), 7.25 (d, J=7.2 Hz, 2H), 2.22 (s, 3H), 2.21 (s, 12H).

ASSAY(S) FOR 11-BETA-HYDROXYSTEROID DEHYDROGENASE ACTIVITY

The in vitro inhibition of recombinant human 11beta-HSD1 was determined as follows.

[$^3$H]-Cortisone with a specific radioactivity of 50 Ci/mmol (ART 743, Lot: 050906) was from American Radiolabeled Chemicals, Inc. (St Louis, Mo.); monoclonal ab to Cortisol (P01-9294M-P, Lot: L-28) was from East Coast Bio., (North Berwick, Me.); Protein A-yttrium silicate, type-1, SPA bead NJ® (RPN-143) was from Amersham LifeSciences, (Piscataway, N.J.); 384 well-Optiplate384® (#6007299) was from PerkinElmer (Boston, Mass.); DPBS, pH 7.4 (14040) is from GIBCO, (Grand Island, N.Y.); carbenoxolone (C4790) is from Sigma, (St Louis, Mo.).

Full length recombinant human 11β-HSD1 cDNAs and the cDNA encoding human 11β-HSD2 were expressed stably in HEK 293 EBNA cells. Cells were grown in DMEM (high glucose) containing MEM non-essential amino acids, L-glutamine, hygromycin B (200 μg/ml), and G-418 (200 μg/ml) in the presence of 10% FBS.

Human 11β-HSD1 transfected HEK 293 EBNA cells were grown to 80% confluency and the cell pellet was quick frozen and stored at –80° C. before purification. Cell paste, 40 g from –80° C. storage, was thawed in water and then 100 ml of homogenization buffer H (0.01 M sodium phosphate pH 6.5 containing 0.25 M sucrose and protease inhibitor cocktail (Roche #1836145 1 tablet per 50 ml) were added to completely thaw the paste. The cell paste suspension was homogenized using a Polytron for 20 seconds to create a homogeneous mixture. Additional buffer H was added to a volume of 300 ml and cells were broken open using a N2-bomb (at 4° C.) in two batches by treating at 500 psi. The extract was centrifuged at 750×g for 30 min. The supernatant was centrifuged at 20,000×g for 30 min. The supernatant was further centrifuged at 105,000×g for 60 min. The 105,000×g pellet was resuspended in buffer H and centrifuged at 105,000×g for 60 min. The microsome pellet was scraped from the bottom of tube and resuspended in 0.01M phosphate buffer, pH 6.5 containing protease inhibitors (Roche #1836145, 1 tablet per 50 ml). Aliquots were stored at –80° C. until needed. The protein concentration was measured by the BioRad method using BSA standard.

Compounds were dissolved in DMSO to obtain 10 mM stock concentrations. From the 10 mM stock, the compounds were diluted in DMSO to achieve the concentrations.

11β-HSD1 SPA Enzyme Assay

11β-HSD1 was assayed by Scintillation Proximity assay in a 384-well PerkinElmer white plate. The dose response of the compounds was determined using 11 half-log dilutions of compound in DMSO in duplicate. To each well, 0.5 μl of compound dilution in DMSO were added. 15 μl of assay buffer (for blanks) or 15 μl of human microsomes in assay buffer were added next and the plates were incubated for 10 min at room temperature. The final microsomal protein concentration was 1.1 μg/assay. Duplicates were in the same plate one row below the other. 10 μl of $^3$H-cortisone (final concentration 40 nM) was added to each well and the plate was spun down to mix and bring down the contents to the bottom of the wells. The plates were incubated at room temperature with gentle shaking for 4 hrs. The reaction was stopped with addition of 10 μl of 10 mM carbenoxolone. Then, 0.5 mg of yttrium silicate SPA beads coupled to anti-cortisol antibody in 20 μl were added to all the wells of plate, which were spun down once more and incubated at room temperature overnight. The plate was read in a TopCount® (1 min/well). Data were uploaded automatically to Tool Set, a Lead Evaluation informatics program for data capture and calculation. Graphs were generated with the Curve Master program.

UTILITIES AND COMBINATIONS

A. Utilities

The compounds of the present invention possess activity as inhibitors of the enzyme 11-beta-hydroxysteroid dehydrogenase type I, and, therefore, may be used in the treatment of diseases associated with 11-beta-hydroxysteroid dehydrogenase type I activity. Via the inhibition of 11-beta-hydroxysteroid dehydrogenase type I, the compounds of the present invention may preferably be employed to inhibit or modulate glucocorticoid production, thereby interrupting or modulating cortisone or cortisol production.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, delayed wound healing, atherosclerosis and its sequelae (acute coronary syndrome, myocardial infarction, angina pectoris, peripheral vascular disease, intermittent claudication), abnormal heart function, myocardial ischemia, stroke, Metabolic Syndrome, hypertension, obesity, dislipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis, Cushing's Disease, Alzheimer's Disease and osteoarthritis.

Metabolic Syndrome or "Syndrome X" is described in Ford et al., *J. Am. Med. Assoc.,* 287:356-359 (2002) and Arbeeny et al., *Curr. Med. Chem.—Imm., Endoc. & Metab. Agents,* 1:1-24 (2001).

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other 11-beta-hydroxysteroid dehydrogenase type I inhibitors or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dislipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, memory enhancing agents, cognition promoting agents and anti-inflammatory agents.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones: ciglitazone, pioglitazone, troglitazone, rosiglitazone; PPAR-gamma agonists; PPAR-alpha agonists; PPAR alpha/gamma dual agonists; SGLT2 inhibitors; dipeptidyl peptidase-IV (DPP4) inhibitors; glucagon-like peptide-1 (GLP-1) receptor agonists; aldose reductase inhibitors; RXR agonists: JTT-501, MCC-555, MX-6054, DRF2593, GI-262570, KRP-297, LG100268; fatty acid oxidation inhibitors: clomoxir, etomoxir; α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316,243, TAK-667, AZ40140; phosphodiesterase inhibitors, both cAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023; and galanin receptor agonists.

Other suitable thiazolidinediones include Mitsubishi's MCC-555 (disclosed in U.S. Pat. No. 5,594,016), Glaxo-Wellcome's GL-262570, englitazone (CP-68722, Pfizer), or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck), as well as those disclosed by Murakami et al., "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", *Diabetes,* 47:1841-1847 (1998), and WO 01/21602, the disclosure of which is incorporated herein by reference, employing dosages as set out therein, which compounds designated as preferred are preferred for use herein.

Suitable alpha2 antagonists also include those disclosed in WO 00/59506, employing dosages as set out herein.

Suitable SGLT2 inhibitors include T-1095, phlorizin, WAY-123783, and those described in WO 01/27128.

Suitable DPP4 inhibitors include saxagliptan, sitagliptan, vildagliptan, and denagliptan.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) receptor agonists include Exenatide (Byetta™), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DAC™).

Other anti-diabetic agents that can be used in combination with compounds of the invention include ergoset and D-chiroinositol.

Suitable anti-ischemic agents include, but are not limited to, those described in the Physicians' Desk Reference and NHE inhibitors, including those disclosed in WO 99/43663.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na$^+$/bile acid cotransporter inhibitors, upregulators of LDL receptor activity, bile acid sequestrants, cholesterol ester transfer protein inhibitors (e.g., CP-529414 (Pfizer)), and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983, and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin, (mevinolin) and related compounds, as disclosed in U.S. Pat. No. 4,231,938, pravastatin, and related compounds, such as disclosed in U.S. Pat. No. 4,346,227, simvastatin, and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772; cerivastatin, as disclosed in U.S. Pat. Nos. 5,006,530 and 5,177,080; atorvastatin, as disclosed in U.S. Pat. Nos. 4,681,893, 5,273,995, 5,385,929 and 5,686,104; atavastatin (Nissan/Sankyo's nisvastatin (NK-104)), as disclosed in U.S. Pat. No. 5,011,930; visastatin (Shionogi-Astra/Zeneca (ZD-4522)) as disclosed in U.S. Pat. No. 5,260,440.

Preferred hypolipidemic agents are pravastatin, lovastatin, simvastatin, atorvastatin, fluvastatin, cerivastatin, atavastatin, and ZD-4522.

The fabric acid derivatives which may be employed in combination with one or more compounds of formula I include fenofibrate, gemfibrozil, clofibrate, bezafibrate, ciprofibrate, clinofibrate, and the like, probucol, and related compounds, as disclosed in U.S. Pat. No. 3,674,836, fenofibrate and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future, 24:9-15 (1999) (Avasimibe); Nicolosi et al., "The ACAT inhibitor, C1-1011 is effective in the prevention and regression of aortic fatty streak area in hamsters", Atherosclerosis (Shannon, Irel.), 137(1): 77-85 (1998); Ghiselli, Giancarlo, "The pharmacological profile of FCE 27677: a novel ACAT inhibitor with potent hypolipidemic activity mediated by selective suppression of the hepatic secretion of ApoB 100-containing lipoprotein", Cardiovasc. Drug Rev., 16(1):16-30 (1998); Smith, C. et al., "RP 73163: a bioavailable alkylsulfinyl-diphenylimidazole ACAT inhibitor", Bioorg. Med. Chem. Lett., 6(1):47-50 (1996); Krause et al., "ACAT inhibitors: physiologic mechanisms for hypolipidemic and anti-atherosclerotic activities in experimental animals", Inflammation: Mediators Pathways, Publisher: CRC, Boca Raton, Fla., Editor(s): Ruffolo, Robert R., Jr.; Hollinger, Mannfred A., pp. 173-198 (1995); Sliskovic et al., "ACAT inhibitors: potential anti-atherosclerotic agents", Curr. Med. Chem., 1(3):204-25 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Chemtracts: Org. Chem., 8(6):359-362 (1995), or TS-962 (Taisho Pharmaceutical Co. Ltd.).

The hypolipidemic agent may be an upregulator of LDL receptor activity, such as MD-700 (Taisho Pharmaceutical Co. Ltd) and LY295427 (Eli Lilly).

Examples of suitable cholesterol absorption inhibitors for use in combination with the compounds of the invention include ezetimibe (Zetia®).

Examples of suitable ileal Na$^+$/bile acid cotransporter inhibitors for use in combination with the compounds of the invention include compounds as disclosed in Drugs of the Future, 24:425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", Brit. J. Pharmacology, 120:1199-1206 (1997), and Cornicelli et al., "15-Lipoxygenase and its Inhibition: A Novel Therapeutic Target for Vascular Disease", Current Pharmaceutical Design, 5:11-20 (1999).

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a cannabinoid receptor 1 antagonist or inverse agonist, a beta 3 adrenergic agonist, a lipase inhibitor, a serotonin (and dopamine) reuptake inhibitor, a thyroid receptor beta drug, and/or an anorectic agent.

Cannabinoid receptor 1 antagonists and inverse agonists which may be optionally employed in combination with compounds of the present invention include rimonabant, SLV 319, CP-945598 (Pfizer), SR-147778 (Sanofi-Aventis), MK0364 (Merck) and those discussed in D. L. Hertzog, *Expert Opin. Ther. Patents*, 14:1435-1452 (2004).

The beta 3 adrenergic agonists which may be optionally employed in combination with compounds of the present invention include AJ9677 (Takeda/Dainippon), L750355 (Merck), or CP331648 (Pfizer), or other known beta 3 agonists, as disclosed in U.S. Pat. Nos. 5,541,204, 5,770,615, 5,491,134, 5,776,983, and 5,488,064, with AJ9677, L750, 355, and CP331648 being preferred.

Examples of lipase inhibitors which may be optionally employed in combination with compounds of the present invention include orlistat or ATL-962 (Alizyme), with orlistat being preferred.

The serotonin (and dopamine) reuptake inhibitor and/or modulator which may be optionally employed in combination with a compound of formula I may be sibutramine, topiramate (Johnson & Johnson), APD-356 (Arena) or axokine (Regeneron), with sibutramine and APD-356 being preferred.

Examples of thyroid receptor beta compounds which may be optionally employed in combination with compounds of the present invention include thyroid receptor ligands, such as those disclosed in WO 97/21993 (U. Cal SF), WO 99/00353 (KaroBio), and WO 00/039077 (KaroBio), with compounds of the KaroBio applications being preferred.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); MCHR1 antagonist (e.g., GSK 856464); galanin receptor antagonists; MCR-4 antagonists (e.g., HP-228); leptin or mimetics; urocortin mimetics, CRF antagonists, and CRF binding proteins (e.g., RU-486, urocortin).

Further, the compounds of the present invention may be used in combination with HIV protease inhibitors, including but not limited to Reyataz® and Kaletra®.

Examples of suitable memory enhancing agents, anti-dementia agents, or cognition promoting agents for use in combination with the compounds of the present invention include, but are not limited to, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, prednisone, acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha, prednisolone, methylprednisolone, dexamethazone, flucatisone, betamethasone, hydrocortisone and beclomethasone.

The aforementioned patents and patent applications are incorporated herein by reference.

The above other therapeutic agents, when employed in combination with the compounds of the present invention may be used, for example, in those amounts indicated in the Physicians' Desk Reference, as in the patents set out above, or as otherwise determined by one of ordinary skill in the art.

The compounds of formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of structure I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

What is claimed is:

1. A compound of formula (I)

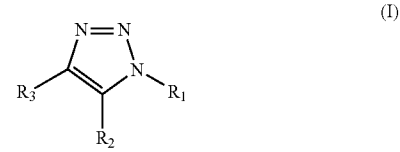

or salts thereof wherein:
$R_1$ is aryl or bicycloalkyl, both of which may be optionally substituted with one or more $R_{1a}$s;
$R_{1a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —C(=O)OH, —C(=O)$OR_{14}$, —$OCF_3$, —$OR_{10}$, —OH, —$OCF_3$, —SH, —$SR_{14}$, —C(=O)$NR_{14}R_{14}$, —$NR_{14}R_{14}$, —C(=O)$R_{14}$, —$NR_{14}$C(=O)$R_{14}$, —OC(=O)$R_{14}$, —C(=$NR_{14}$) $NR_{14}R_{14}$, —NHC(=$NR_{14}$)$NR_{14}R_{14}$, —S(=O)$R_{14}$, —$NR_{14}$C(=O)$OR_{10}$, —OC(=O)$NR_{14}R_{14}$, —$NR_{14}$C(=O)$NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;
$R_2$ is unsubstituted $C_{1-4}$ alkyl;
$R_3$ is bicycloalkyl, which may be optionally substituted with one or more $R_{3a}$'s;
$R_{3a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —CN, —$NO_2$, —C(=O)OH, —C(=O)$OR_{14}$, —$OCF_3$, —$OR_{10}$, —OH, —$OCF_3$, —SH, —$SR_{14}$, —C(=O)$NR_{14}R_{14}$, —$NR_{14}R_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_8$, at each occurrence, is independently alkyl, aryl or heterocyclyl;

R$_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —C(=)R$_{15}$, —NR$_{15}$R$_{15}$, —NHC(=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl;

provided that:
the compound is not a compound of the following structure:

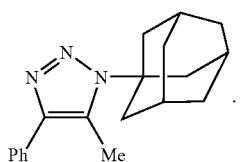

2. The compound of claim 1, wherein R$_1$ is aryl, which may be optionally substituted with one or more R$_{1a}$'s.

3. The compound of claim 2, wherein R$_1$ is a monocyclic aryl, which may be optionally substituted with one or more R$_{1a}$'s.

4. The compound of claim 1, wherein R$_1$ is a monocyclic aryl, which may be optionally substituted with one or more R$_{1a}$'s and R$_3$ is a [2,2,2]bicycloalkyl, which may be optionally substituted with one or more R$_{3a}$'s.

5. The compound of claim 1, wherein R$_1$ is bicycloalkyl, which may be optionally substituted with one or more R$_{1a}$'s.

6. The compound of claim 1, wherein:
R$_1$ is aryl or bicycloalkyl, both of which may be optionally substituted with one or more R$_{1a}$s;

R$_{1a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —NR$_{14}$C(=O)OR$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_2$ is unsubstituted C$_{1-3}$ alkyl;

R$_3$ is bicycloalkyl, which may be optionally substituted with one or more R$_{3a}$s;

R$_{3a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O)OR$_{10}$, —NR$_{15}$S(O$_2$)R$_8$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_8$, at each occurrence, is independently alkyl, aryl or heterocyclyl;

R$_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —C(=NR$_{15}$)NR$_{15}$R$_{15}$, —NHC(=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

7. The compound of claim 1, wherein:

R$_1$ is a monocyclic aryl or bicycloalkyl, both of which may be optionally substituted with one or more R$_{1a}$'s;

R$_{1a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —NR$_{14}$C(=O)OR$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_2$ is unsubstituted C$_{1-3}$ alkyl;

R$_3$ is bicycloalkyl, which may be optionally substituted with one or more R$_{3a}$ s;

R$_{3a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_8$, at each occurrence, is independently alkyl, aryl or heterocyclyl;

R$_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

R$_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 R$_{14a}$;

R$_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —C(=NR$_{15}$)NR$_{15}$R$_{15}$, —NHC(=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and R$_{15}$, at each occurrence, is independently selected from hydrogen, alkyl, cycloalkyl, aryl or arylalkyl.

8. The compound of claim 1, wherein:

R$_1$ is a monocyclic aryl or bicycloalkyl, both of which may be optionally substituted with one or more R$_{1a}$'s;

R$_{1a}$, at each occurrence, is independently selected from alkyl, haloalkyl, aryl, alkynyl, cycloalkyl, cycloalkylalkyl, heterocyclyl, heterocyclylalkyl, halo, —NH$_2$, —OCF$_3$, —OR$_{10}$, —OCF$_3$, —C(=O)NR$_{14}$R$_{14}$, —NR$_{14}$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —NR$_{14}$C(=O)OR$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_2$ is unsubstituted C$_{1-3}$ alkyl;

R$_3$ is bicycloalkyl, which may be optionally substituted with one or more R$_{3a}$'s;

R$_{3a}$, at each occurrence, is independently selected from alkyl, haloalkyl, aryl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 R$_{10a}$;

R$_8$, at each occurrence, is independently alkyl, aryl or heterocyclyl;

R$_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 R$_{10a}$, and the heterocyclyl contains 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —$NO_2$, —$C(=O)OH$, —$C(=O)OR_{15}$, —$OCF_3$, —$OR_{15}$, —$OH$, —$SH$, —$SR_{15}$, —$C(=O)NR_{15}R_{15}$, —$NR_{15}R_{15}$, —$S(O)_2NR_{15}R_{15}$, —$NR_{15}S(O)_2CF_3$, —$C(=O)NR_{15}S(O)_2R_{15}$, —$S(O)_2NR_{15}C(=O)OR_{15}$, —$S(O)_2NR_{15}C(=O)NR_{15}R_{15}$, —$C(=O)NR_{15}S(O)_2CF_3$, —$C(=O)R_{15}$, —$NR_{15}C(=O)R_{15}$, —$OC(=O)R_{15}$, —$C(=NR_{15})NR_{15}R_{15}$, —$NHC(=NR_{15})NR_{15}R_{15}$, —$S(=O)R_{15}$, —$S(O)_2R_{15}$, —$NR_{15}C(=O)OR_8$, —$NR_{15}S(O_2)R_8$ or arylalkyl; and $R_{15}$, at each occurrence, is independently selected from hydrogen, alkyl, cycloalkyl, aryl or arylalkyl.

9. The compound of claim 1, wherein:

$R_1$ is a monocyclic aryl or bicycloalkyl, both of which may be optionally substituted with one or more $R_{1a}$'s;

$R_{1a}$, at each occurrence, is independently selected from alkyl, haloalkyl, aryl, alkynyl, cycloalkyl, cycloalkylalkyl, heterocyclyl, heterocyclylalkyl, halo, —$NH_2$, —$OCF_3$, —$OR_{10}$, —$OCF_3$, —$C(=O)NR_{14}R_{14}$, —$NR_{14}R_{14}$, —$C(=O)R_{14}$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$NR_{14}C(=O)OR_{10}$, —$OC(=O)NR_{14}R_{14}$, —$NR_{14}C(=O)NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_2$ is $C_{1-3}$ alkyl;

$R_3$ is bicycloalkyl, which may be optionally substituted with one or more $R_{3a}$'s;

$R_{3a}$, at each occurrence, is independently selected from alkyl, haloalkyl, aryl, alkynyl, cycloalkyl, cycloalkylalkyl, heterocyclyl, heterocyclylalkyl, halo, —$NH_2$, —$CN$, —$NO_2$, —$C(=O)OH$, —$C(=O)OR_{14}$, —$OCF_3$, —$OR_{10}$, —$OH$, —$OCF_3$, —$SH$, —$SR_{14}$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{10}$, —$S(O)_2NR_{14}C(=O)OR_{10}$, —$S(O)_2NR_{14}C(=O)NR_{14}R_{14}$, —$C(=O)NR_{14}S(O)_2R_{14}$, —$C(=O)R_{14}$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$OS(O)_2R_{14}$, —$NR_{14}C(=O)OR_{10}$, —$NR_{14}S(O_2)R_8$, —$OC(=O)NR_{14}R_{14}$, —$NR_{14}C(=O)NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_8$, at each occurrence, is independently alkyl, aryl or heterocyclyl;

$R_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —$CN$, —$NO_2$, —$OCF_3$, —$OR_{14}$, —$OH$, —$SH$, —$SR_{14}$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{14}$, —$S(O)_2NR_{14}C(=O)OR_{14}$, —$S(O)_2NR_{14}C(=O)NR_{14}R_{14}$, —$C(=O)NR_{14}S(O)_2CF_3$, —$C(=O)R_{14}$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$NR_{14}C(=O)OR_8$, —$NR_{14}S(O_2)R_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —$NH_2$, —$NO_2$, —$C(=O)OH$, —$C(=O)OR_{15}$, —$OCF_3$, —$OR_{15}$, —$OH$, —$SH$, —$SR_{15}$, —$C(=O)NR_{15}R_{15}$, —$NR_{15}R_{15}$, —$S(O)_2NR_{15}R_{15}$, —$NR_{15}S(O)_2CF_3$, —$C(=O)NR_{15}S(O)_2R_{15}$, —$S(O)_2NR_{15}C(=O)OR_{15}$, —$S(O)_2NR_{15}C(=O)NR_{15}R_{15}$, —$C(=O)NR_{15}S(O)_2CF_3$, —$C(=O)R_{15}$, —$NR_{15}C(=O)R_{15}$, —$OC(=O)R_{15}$, —$C(=NR_{15})NR_{15}R_{15}$, —$NHC(=NR_{15})NR_{15}R_{15}$, —$S(=O)R_{15}$, —$S(O)_2R_{15}$, —$NR_{15}C(=O)OR_8$, —$NR_{15}S(O_2)R_8$ or arylalkyl; and $R_{15}$, at each occurrence, is independently selected from hydrogen, alkyl, cycloalkyl, aryl or arylalkyl.

10. The compound of claim 1, wherein:

$R_1$ is phenyl or bicycloalkyl, both of which may be optionally substituted with one or more $R_{1a}$'s;

$R_{1a}$, at each occurrence, is independently selected from alkyl, haloalkyl, aryl, alkynyl, cycloalkyl, cycloalkylalkyl, heterocyclyl, heterocyclylalkyl, halo, —$NH_2$, —$OCF_3$, —$OR_{10}$, —$OCF_3$, —$C(=O)NR_{14}R_{14}$, —$NR_{14}R_{14}$, —$C(=O)R_{14}$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$NR_{14}C(=O)OR_{10}$, —$OC(=O)NR_{14}R_{14}$, —$NR_{14}C(=O)NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_2$ is $C_{1-3}$ alkyl;

$R_3$ is bicycloalkyl, which may be optionally substituted with one or more $R_{3a}$'s;

$R_{3a}$, at each occurrence, is independently selected from alkyl, haloalkyl, aryl, alkynyl, cycloalkyl, cycloalkylalkyl, heterocyclyl, heterocyclylalkyl, halo, —$NH_2$, —$CN$, —$NO_2$, —$C(=O)OH$, —$C(=O)OR_{14}$, —$OCF_3$, —$OR_{10}$, —$OH$, —$OCF_3$, —$SH$, —$SR_{14}$, —$C(=O)NR_{14}R_{14}$, —$NR_{14}R_{14}$, —$S(O)_2NR_{14}R_{14}$, —$NR_{14}S(O)_2CF_3$, —$C(=O)NR_{14}S(O)_2R_{10}$, —$S(O)_2NR_{14}C(=O)OR_{10}$, —$S(O)_2NR_{14}C(=O)NR_{14}R_{14}$, —$C(=O)NR_{14}S(O)_2R_{14}$, —$C(=O)R_{14}$, —$NR_{14}C(=O)R_{14}$, —$OC(=O)R_{14}$, —$C(=NR_{14})NR_{14}R_{14}$, —$NHC(=NR_{14})NR_{14}R_{14}$, —$S(=O)R_{14}$, —$S(O)_2R_{14}$, —$OS(O)_2R_{14}$, —$NR_{14}C(=O)OR_{10}$, —$NR_{14}S(O_2)R_8$, —$OC(=O)NR_{14}R_{14}$, —$NR_{14}C(=O)NR_{14}R_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_8$, at each occurrence, is independently alkyl, aryl or heterocyclyl;

$R_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —C(=NR$_{15}$)NR$_{15}$R$_{15}$, —NHC(=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and $R_{15}$, at each occurrence, is independently selected from hydrogen, alkyl, cycloalkyl, aryl or arylalkyl.

11. The compound of claim 1, wherein:

$R_1$ is phenyl or bicycloalkyl, both of which may be optionally substituted with one or more $R_{1a}$'s;

$R_{1a}$, at each occurrence, is independently selected from alkyl, haloalkyl, aryl, alkynyl, cycloalkyl, cycloalkylalkyl, heterocyclyl, heterocyclylalkyl, halo, —NH$_2$, —OCF$_3$, —OR$_{10}$, —OCF$_3$, —C(=O)NR$_{14}$R$_{14}$, —NR$_{14}$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —NR$_{14}$C(=O)OR$_{10}$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_2$ is methyl;

$R_3$ is bicycloalkyl, which may be optionally substituted with one or more $R_{3a}$'s;

$R_{3a}$, at each occurrence, is independently selected from alkyl, haloalkyl, aryl, alkynyl, cycloalkyl, cycloalkylalkyl, heterocyclyl, heterocyclylalkyl, halo, —NH$_2$, —CN, —NO$_2$, —C(=O)OH, —C(=O)OR$_{14}$, —OCF$_3$, —OR$_{10}$, —OH, —OCF$_3$, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{10}$, —S(O)$_2$NR$_{14}$C(=O)OR$_{10}$, —S(O)$_2$NR$_{14}$C(=O)NR$_{14}$R$_{14}$, —C(=O)NR$_{14}$S(O)$_2$R$_{14}$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —OS(O)$_2$R$_{14}$, —NR$_{14}$C(=O)OR$_{10}$, —NR$_{14}$S(O$_2$)R$_8$, —OC(=O)NR$_{14}$R$_{14}$, —NR$_{14}$C(=O)NR$_{14}$R$_{14}$ or arylalkyl, wherein the alkyl, aryl, cycloalkyl, cycloalkylalkyl, heterocyclyl, and heterocyclylalkyl may be optionally substituted with 0-3 $R_{10a}$;

$R_8$, at each occurrence, is independently alkyl, aryl or heterocyclyl;

$R_{10}$, at each occurrence, is independently selected from alkyl, cycloalkyl, alkenyl, alkynyl, aryl, arylalkyl or heterocyclyl, wherein the alkyl, cycloalkyl, aryl, arylalkyl or heterocyclyl may be optionally substituted with 0-3 $R_{10a}$, and the heterocyclyl contains 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —CN, —NO$_2$, —OCF$_3$, —OR$_{14}$, —OH, —SH, —SR$_{14}$, —C(=O)NR$_{14}$R$_{14}$, —NR$_{14}$R$_{14}$, —S(O)$_2$NR$_{14}$R$_{14}$, —NR$_{14}$S(O)$_2$CF$_3$, —C(=O)NR$_{14}$S(O)$_2$R$_{14}$, —S(O)$_2$NR$_{14}$C(=O)OR$_{14}$, —S(O)$_2$NR$_{14}$C(=O)NR$_{14}$R$_{14}$, —C(=O)NR$_{14}$S(O)$_2$CF$_3$, —C(=O)R$_{14}$, —NR$_{14}$C(=O)R$_{14}$, —OC(=O)R$_{14}$, —C(=NR$_{14}$)NR$_{14}$R$_{14}$, —NHC(=NR$_{14}$)NR$_{14}$R$_{14}$, —S(=O)R$_{14}$, —S(O)$_2$R$_{14}$, —NR$_{14}$C(=O)OR$_8$, —NR$_{14}$S(O$_2$)R$_8$ or arylalkyl;

$R_{14}$, at each occurrence, is independently selected from hydrogen, alkyl, cycloalkyl, aryl or arylalkyl, wherein the alkyl, cycloalkyl, aryl or arylalkyl may be optionally substituted with 0-3 $R_{14a}$;

$R_{14a}$, at each occurrence, is independently selected from alkyl, haloalkyl, aryl, alkenyl, alkynyl, cycloalkyl, cycloalkylalkyl, heterocyclyl, heterocyclylalkyl, halo, —NH$_2$, —NO$_2$, —C(=O)OH, —C(=O)OR$_{15}$, —OCF$_3$, —OR$_{15}$, —OH, —SH, —SR$_{15}$, —C(=O)NR$_{15}$R$_{15}$, —NR$_{15}$R$_{15}$, —S(O)$_2$NR$_{15}$R$_{15}$, —NR$_{15}$S(O)$_2$CF$_3$, —C(=O)NR$_{15}$S(O)$_2$R$_{15}$, —S(O)$_2$NR$_{15}$C(=O)OR$_{15}$, —S(O)$_2$NR$_{15}$C(=O)NR$_{15}$R$_{15}$, —C(=O)NR$_{15}$S(O)$_2$CF$_3$, —C(=O)R$_{15}$, —NR$_{15}$C(=O)R$_{15}$, —OC(=O)R$_{15}$, —C(=NR$_{15}$)NR$_{15}$R$_{15}$, —NHC(=NR$_{15}$)NR$_{15}$R$_{15}$, —S(=O)R$_{15}$, —S(O)$_2$R$_{15}$, —NR$_{15}$C(=O)OR$_8$, —NR$_{15}$S(O$_2$)R$_8$ or arylalkyl; and $R_{15}$, at each occurrence, is independently selected from hydrogen, alkyl, cycloalkyl, aryl or arylalkyl.

12. A compound selected from the group consisting of:

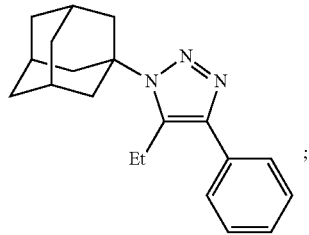

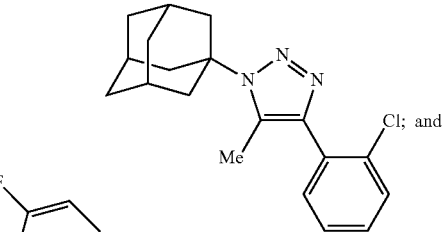

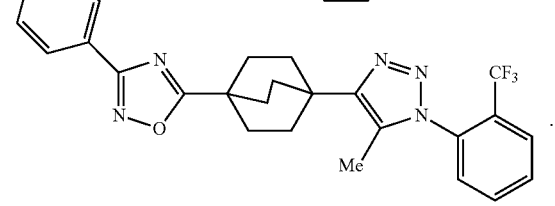

13. A pharmaceutical composition comprising at least one compound of claim 1 and a pharmaceutically acceptable carrier.

* * * * *

UNITED STATES PATENT AND TRADEMARK OFFICE
CERTIFICATE OF CORRECTION

PATENT NO.          : 8,263,630 B2                                              Page 1 of 1
APPLICATION NO.     : 12/867262
DATED               : September 11, 2012
INVENTOR(S)         : James J. Li It is certified that error appears in the above-identified patent and that said Letters Patent is hereby corrected as shown below:

In the Claims:

Claim 1:

Column 34, line 45, change "$R_{1a}s;$" to -- $R_{1a}$'s; --.

Column 35, line 46, change "—C(=)$R_{15}$, —$NR_{15}R_{15}$," to -- —C(=$NR_{15}$)$NR_{15}R_{15}$, --.

Claim 6:

Column 36, line 9, change "$R_{1a}s;$" to -- $R_{1a}$'s; --.

Column 36, line 24, change "$R_{3a}s;$" to -- $R_{3a}$'s; --.

Claim 7:

Column 37, line 30, change "$R_{3a}s;$" to -- $R_{3a}$'s; --.

Signed and Sealed this
Ninth Day of December, 2014

Michelle K. Lee
*Deputy Director of the United States Patent and Trademark Office*